US007157263B2

(12) United States Patent
Munk et al.

(10) Patent No.: US 7,157,263 B2
(45) Date of Patent: Jan. 2, 2007

(54) LIPASE VARIANTS

(75) Inventors: Signe Munk, Kobenhavn K (DK); Jesper Vind, Vaerlose (DK); Kim Borch, Birkerod (DK); Shamkant Anant Patkar, Lyngby (DK); Sanne O. Schroder Glad, Ballerup (DK); Allan Svendsen, Horsholm (DK)

(73) Assignee: Novozymes A/S, Bagsvaerd (DK)

( * ) Notice: Subject to any disclaimer, the term of this patent is extended or adjusted under 35 U.S.C. 154(b) by 269 days.

(21) Appl. No.: 10/250,727

(22) PCT Filed: Feb. 7, 2002

(86) PCT No.: PCT/DK02/00084

§ 371 (c)(1),
(2), (4) Date: Jul. 3, 2003

(87) PCT Pub. No.: WO02/062973

PCT Pub. Date: Aug. 15, 2002

(65) Prior Publication Data

US 2004/0053360 A1 Mar. 18, 2004

Related U.S. Application Data

(60) Provisional application No. 60/269,140, filed on Feb. 15, 2001.

(30) Foreign Application Priority Data

Feb. 7, 2001 (DK) .............................. 2001 00195

(51) Int. Cl.
*C12N 9/20* (2006.01)

(52) U.S. Cl. ..................... 435/198; 435/18; 435/252.3; 435/320.1; 536/23.2

(58) Field of Classification Search .................. 435/18, 435/198, 252.3, 320.1; 536/23.2
See application file for complete search history.

(56) References Cited

U.S. PATENT DOCUMENTS

| | | | | |
|---|---|---|---|---|
| 5,223,169 | A | 6/1993 | El-Sayed et al. | |
| 5,869,438 | A | 2/1999 | Svendsen et al. | |
| 5,976,855 | A | 11/1999 | Svendsen et al. | |
| 6,495,357 | B1 * | 12/2002 | Fuglsang et al. | ........... 435/198 |

FOREIGN PATENT DOCUMENTS

| | | |
|---|---|---|
| EP | 0 430 315 | 9/1990 |
| EP | 0 258 068 | 8/1994 |
| EP | 0 305 216 | 8/1995 |
| WO | WO 92/19726 | 11/1992 |
| WO | WO 97/04079 | 2/1997 |
| WO | WO 97/07202 | 2/1997 |
| WO | WO 00/32758 | 6/2000 |
| WO | WO 00/60063 | 10/2000 |

OTHER PUBLICATIONS

Sequence search alignment between Applicants SEQ ID No. 2 and accession No. AAW14423 fro WO9704079.*
Sequence search alignment between Applicants SEQ ID No. 2 and SEQ ID No. 16 from USP 6,495,357.*
Toshihiro et al; Cloning and Nucleotide Sequence of cDNA Encoding a Lipase from *Fusarium heterosporum*, J. Biochem, vol. 116, pp. 536-540, (1994).

* cited by examiner

*Primary Examiner*—Tekchand Saidha
(74) *Attorney, Agent, or Firm*—Elias J. Lambiris

(57) ABSTRACT

Attaching a peptide extension to the C-terminal amino acid of a lipase re-duces the tendency to form odor. This may lead to lipase variants with a reduced odor generation when washing textile soiled with fat which includes relatively short-chain fatty acyl groups (e.g. up to C8) such as dairy stains containing butter fat or tropical oils such as coconut oil or palm kernel oil.

18 Claims, No Drawings

SEQUENCE LISTING

```
<160> NUMBER OF SEQ ID NOS: 12

<210> SEQ ID NO 1
<211> LENGTH: 918
<212> TYPE: DNA
<213> ORGANISM: Thermomyces lanuginosus
<220> FEATURE:
<221> NAME/KEY: CDS
<222> LOCATION: (1)..(873)
<220> FEATURE:
<221> NAME/KEY: sig_peptide
<222> LOCATION: (1)..(66)
<220> FEATURE:
<221> NAME/KEY: mat_peptide
<222> LOCATION: (67)..()

<400> SEQUENCE: 1

atg agg agc tcc ctt gtg ctg ttc ttt gtc tct gcg tgg acg gcc ttg       48
Met Arg Ser Ser Leu Val Leu Phe Phe Val Ser Ala Trp Thr Ala Leu
        -20                 -15                 -10

gcc agt cct att cgt cga gag gtc tcg cag gat ctg ttt aac cag ttc       96
Ala Ser Pro Ile Arg Arg Glu Val Ser Gln Asp Leu Phe Asn Gln Phe
    -5              -1  1               5                   10

aat ctc ttt gca cag tat tct gca gcc gca tac tgc gga aaa aac aat      144
Asn Leu Phe Ala Gln Tyr Ser Ala Ala Ala Tyr Cys Gly Lys Asn Asn
                15                  20                  25

gat gcc cca gct ggt aca aac att acg tgc acg gga aat gcc tgc ccc      192
Asp Ala Pro Ala Gly Thr Asn Ile Thr Cys Thr Gly Asn Ala Cys Pro
            30                  35                  40

gag gta gag aag gcg gat gca acg ttt ctc tac tcg ttt gaa gac tct      240
Glu Val Glu Lys Ala Asp Ala Thr Phe Leu Tyr Ser Phe Glu Asp Ser
        45                  50                  55

gga gtg ggc gat gtc acc ggc ttc ctt gct ctc gac aac acg aac aaa      288
Gly Val Gly Asp Val Thr Gly Phe Leu Ala Leu Asp Asn Thr Asn Lys
    60                  65                  70

ttg atc gtc ctc tct ttc cgt ggc tct cgt tcc ata gag aac tgg atc      336
Leu Ile Val Leu Ser Phe Arg Gly Ser Arg Ser Ile Glu Asn Trp Ile
75                  80                  85                  90

ggg aat ctt aac ttc gac ttg aaa gaa ata aat gac att tgc tcc ggc      384
Gly Asn Leu Asn Phe Asp Leu Lys Glu Ile Asn Asp Ile Cys Ser Gly
                95                  100                 105

tgc agg gga cat gac ggc ttc act tcg tcc tgg agg tct gta gcc gat      432
Cys Arg Gly His Asp Gly Phe Thr Ser Ser Trp Arg Ser Val Ala Asp
            110                 115                 120

acg tta agg cag aag gtg gag gat gct gtg agg gag cat ccc gac tat      480
Thr Leu Arg Gln Lys Val Glu Asp Ala Val Arg Glu His Pro Asp Tyr
        125                 130                 135

cgc gtg gtg ttt acc gga cat agc ttg ggt ggt gca ttg gca act gtt      528
Arg Val Val Phe Thr Gly His Ser Leu Gly Gly Ala Leu Ala Thr Val
    140                 145                 150

gcc gga gca gac ctg cgt gga aat ggg tat gat atc gac gtg ttt tca      576
Ala Gly Ala Asp Leu Arg Gly Asn Gly Tyr Asp Ile Asp Val Phe Ser
155                 160                 165                 170

tat ggc gcc ccc cga gtc gga aac agg gct ttt gca gaa ttc ctg acc      624
Tyr Gly Ala Pro Arg Val Gly Asn Arg Ala Phe Ala Glu Phe Leu Thr
                175                 180                 185

gta cag acc ggc gga aca ctc tac cgc att acc cac acc aat gat att      672
Val Gln Thr Gly Gly Thr Leu Tyr Arg Ile Thr His Thr Asn Asp Ile
            190                 195                 200
```

-continued

```
gtc cct aga ctc ccg ccg cgc gaa ttc ggt tac agc cat tct agc cca      720
Val Pro Arg Leu Pro Pro Arg Glu Phe Gly Tyr Ser His Ser Ser Pro
        205                 210                 215

gag tac tgg atc aaa tct gga acc ctt gtc ccc gtc acc cga aac gat      768
Glu Tyr Trp Ile Lys Ser Gly Thr Leu Val Pro Val Thr Arg Asn Asp
    220                 225                 230

atc gtg aag ata gaa ggc atc gat gcc acc ggc ggc aat aac cag cct      816
Ile Val Lys Ile Glu Gly Ile Asp Ala Thr Gly Gly Asn Asn Gln Pro
235                 240                 245                 250

aac att ccg gat atc cct gcg cac cta tgg tac ttc ggg tta att ggg      864
Asn Ile Pro Asp Ile Pro Ala His Leu Trp Tyr Phe Gly Leu Ile Gly
                255                 260                 265

aca tgt ctt tagtggccgg cgcggctggg tccgactcta gcgagctcga gatct        918
Thr Cys Leu


<210> SEQ ID NO 2
<211> LENGTH: 291
<212> TYPE: PRT
<213> ORGANISM: Thermomyces lanuginosus

<400> SEQUENCE: 2

Met Arg Ser Ser Leu Val Leu Phe Phe Val Ser Ala Trp Thr Ala Leu
        -20                 -15                 -10

Ala Ser Pro Ile Arg Arg Glu Val Ser Gln Asp Leu Phe Asn Gln Phe
    -5                  -1  1               5                   10

Asn Leu Phe Ala Gln Tyr Ser Ala Ala Ala Tyr Cys Gly Lys Asn Asn
                15                  20                  25

Asp Ala Pro Ala Gly Thr Asn Ile Thr Cys Thr Gly Asn Ala Cys Pro
            30                  35                  40

Glu Val Glu Lys Ala Asp Ala Thr Phe Leu Tyr Ser Phe Glu Asp Ser
        45                  50                  55

Gly Val Gly Asp Val Thr Gly Phe Leu Ala Leu Asp Asn Thr Asn Lys
    60                  65                  70

Leu Ile Val Leu Ser Phe Arg Gly Ser Arg Ser Ile Glu Asn Trp Ile
75                  80                  85                  90

Gly Asn Leu Asn Phe Asp Leu Lys Glu Ile Asn Asp Ile Cys Ser Gly
                95                  100                 105

Cys Arg Gly His Asp Gly Phe Thr Ser Ser Trp Arg Ser Val Ala Asp
            110                 115                 120

Thr Leu Arg Gln Lys Val Glu Asp Ala Val Arg Glu His Pro Asp Tyr
        125                 130                 135

Arg Val Val Phe Thr Gly His Ser Leu Gly Gly Ala Leu Ala Thr Val
    140                 145                 150

Ala Gly Ala Asp Leu Arg Gly Asn Gly Tyr Asp Ile Asp Val Phe Ser
155                 160                 165                 170

Tyr Gly Ala Pro Arg Val Gly Asn Arg Ala Phe Ala Glu Phe Leu Thr
                175                 180                 185

Val Gln Thr Gly Gly Thr Leu Tyr Arg Ile Thr His Thr Asn Asp Ile
            190                 195                 200

Val Pro Arg Leu Pro Pro Arg Glu Phe Gly Tyr Ser His Ser Ser Pro
        205                 210                 215

Glu Tyr Trp Ile Lys Ser Gly Thr Leu Val Pro Val Thr Arg Asn Asp
    220                 225                 230

Ile Val Lys Ile Glu Gly Ile Asp Ala Thr Gly Gly Asn Asn Gln Pro
235                 240                 245                 250
```

-continued

```
Asn Ile Pro Asp Ile Pro Ala His Leu Trp Tyr Phe Gly Leu Ile Gly
                255                 260                 265

Thr Cys Leu


<210> SEQ ID NO 3
<211> LENGTH: 1083
<212> TYPE: DNA
<213> ORGANISM: Talaromyces thermophilus
<220> FEATURE:
<221> NAME/KEY: CDS
<222> LOCATION: (1)..(67)
<220> FEATURE:
<221> NAME/KEY: mat_peptide
<222> LOCATION: (67)..()
<220> FEATURE:
<221> NAME/KEY: CDS
<222> LOCATION: (139)..(307)
<220> FEATURE:
<221> NAME/KEY: CDS
<222> LOCATION: (370)..(703)
<220> FEATURE:
<221> NAME/KEY: CDS
<222> LOCATION: (778)..(1080)

<400> SEQUENCE: 3

atg agg agc tcg ctc gtg ctg ttc ttc gtt tct gcg tgg acg gcc ttg       48
Met Arg Ser Ser Leu Val Leu Phe Phe Val Ser Ala Trp Thr Ala Leu
        -20                 -15                 -10

gcc agt cct gtc cga cga g gtatgtaaat cacggggtat acttttcatg           97
Ala Ser Pro Val Arg Arg
    -5              -1

cattgcatgt cgaacctgct gtactaagat tgcgcgcaca g ag  gtc tcg cag gat    152
                                              Glu Val Ser Gln Asp
                                                              5

ctg ttt gac cag ttc aac ctc ttt gcg cag tac tcg gcg gcc gca tac      200
Leu Phe Asp Gln Phe Asn Leu Phe Ala Gln Tyr Ser Ala Ala Ala Tyr
                10                  15                  20

tgc gcg aag aac aac gat gcc ccg gca ggt ggg aac gta acg tgc agg      248
Cys Ala Lys Asn Asn Asp Ala Pro Ala Gly Gly Asn Val Thr Cys Arg
            25                  30                  35

gga agt att tgc ccc gag gta gag aag gcg gat gca acg ttt ctc tac      296
Gly Ser Ile Cys Pro Glu Val Glu Lys Ala Asp Ala Thr Phe Leu Tyr
        40                  45                  50

tcg ttt gag ga  gtaggtgtca acaagagtac aggcacccgt agtagaaata          347
Ser Phe Glu Asp
    55

gcagactaac tgggaaatgt ag t tct gga gtt ggc gat gtc acc ggg ttc       397
                           Ser Gly Val Gly Asp Val Thr Gly Phe
                                   60                  65

ctt gct ctc gac aac acg aac aga ctg atc gtc ctc tct ttc cgc ggc      445
Leu Ala Leu Asp Asn Thr Asn Arg Leu Ile Val Leu Ser Phe Arg Gly
            70                  75                  80

tct cgt tcc ctg gaa aac tgg atc ggg aat atc aac ttg gac ttg aaa      493
Ser Arg Ser Leu Glu Asn Trp Ile Gly Asn Ile Asn Leu Asp Leu Lys
        85                  90                  95

gga att gac gac atc tgc tct ggc tgc aag gga cat gac ggc ttc act      541
Gly Ile Asp Asp Ile Cys Ser Gly Cys Lys Gly His Asp Gly Phe Thr
    100                 105                 110

tcc tcc tgg agg tcc gtt gcc aat acc ttg act cag caa gtg cag aat      589
Ser Ser Trp Arg Ser Val Ala Asn Thr Leu Thr Gln Gln Val Gln Asn
115                 120                 125                 130

gct gtg agg gag cat ccc gac tac cgc gtc gtc ttc act ggg cac agc      637
Ala Val Arg Glu His Pro Asp Tyr Arg Val Val Phe Thr Gly His Ser
                135                 140                 145
```

-continued

```
ttg ggt ggt gca ttg gca act gtg gcc ggg gca tct ctg cgt gga aat      685
Leu Gly Gly Ala Leu Ala Thr Val Ala Gly Ala Ser Leu Arg Gly Asn
            150                 155                 160

ggg tac gat ata gat gtg gtatgtagga aaaatgatcc ccgtggagcg             733
Gly Tyr Asp Ile Asp Val
        165

gtcatgtgga aatgtgcagg ggtgtctaat acacagacca acag ttc tca tat ggc     789
                                                 Phe Ser Tyr Gly
                                                     170

gct ccc cgc gtc gga aac agg gct ttt gcg gaa ttc ctg acc gca cag      837
Ala Pro Arg Val Gly Asn Arg Ala Phe Ala Glu Phe Leu Thr Ala Gln
        175                 180                 185

acc ggc ggc acc ttg tac cgc atc acc cac acc aat gat att gtc ccc      885
Thr Gly Gly Thr Leu Tyr Arg Ile Thr His Thr Asn Asp Ile Val Pro
    190                 195                 200

aga ctc ccg cca cgc gaa ttg ggt tac agc cat tct agc cca gag tat      933
Arg Leu Pro Pro Arg Glu Leu Gly Tyr Ser His Ser Ser Pro Glu Tyr
205                 210                 215                 220

tgg atc acg tct gga acc ctc gtc cca gtg acc aag aac gat atc gtc      981
Trp Ile Thr Ser Gly Thr Leu Val Pro Val Thr Lys Asn Asp Ile Val
                225                 230                 235

aag gtg gag ggc atc gat tcc acc gat gga aac aac cag cca aat acc     1029
Lys Val Glu Gly Ile Asp Ser Thr Asp Gly Asn Asn Gln Pro Asn Thr
            240                 245                 250

ccg gac att gct gcg cac cta tgg tac ttc ggg tca atg gcg acg tgt     1077
Pro Asp Ile Ala Ala His Leu Trp Tyr Phe Gly Ser Met Ala Thr Cys
        255                 260                 265

ttg taa                                                             1083
Leu


<210> SEQ ID NO 4
<211> LENGTH: 291
<212> TYPE: PRT
<213> ORGANISM: Talaromyces thermophilus

<400> SEQUENCE: 4

Met Arg Ser Ser Leu Val Leu Phe Phe Val Ser Ala Trp Thr Ala Leu
        -20                 -15                 -10

Ala Ser Pro Val Arg Arg Glu Val Ser Gln Asp Leu Phe Asp Gln Phe
    -5                  -1  1               5                   10

Asn Leu Phe Ala Gln Tyr Ser Ala Ala Ala Tyr Cys Ala Lys Asn Asn
                15                  20                  25

Asp Ala Pro Ala Gly Gly Asn Val Thr Cys Arg Gly Ser Ile Cys Pro
            30                  35                  40

Glu Val Glu Lys Ala Asp Ala Thr Phe Leu Tyr Ser Phe Glu Asp Ser
        45                  50                  55

Gly Val Gly Asp Val Thr Gly Phe Leu Ala Leu Asp Asn Thr Asn Arg
    60                  65                  70

Leu Ile Val Leu Ser Phe Arg Gly Ser Arg Ser Leu Glu Asn Trp Ile
75                  80                  85                  90

Gly Asn Ile Asn Leu Asp Leu Lys Gly Ile Asp Asp Ile Cys Ser Gly
                95                  100                 105

Cys Lys Gly His Asp Gly Phe Thr Ser Ser Trp Arg Ser Val Ala Asn
            110                 115                 120

Thr Leu Thr Gln Gln Val Gln Asn Ala Val Arg Glu His Pro Asp Tyr
        125                 130                 135

Arg Val Val Phe Thr Gly His Ser Leu Gly Gly Ala Leu Ala Thr Val
    140                 145                 150
```

-continued

```
Ala Gly Ala Ser Leu Arg Gly Asn Gly Tyr Asp Ile Asp Val Phe Ser
155                 160                 165                 170

Tyr Gly Ala Pro Arg Val Gly Asn Arg Ala Phe Ala Glu Phe Leu Thr
                175                 180                 185

Ala Gln Thr Gly Gly Thr Leu Tyr Arg Ile Thr His Thr Asn Asp Ile
            190                 195                 200

Val Pro Arg Leu Pro Pro Arg Glu Leu Gly Tyr Ser His Ser Ser Pro
        205                 210                 215

Glu Tyr Trp Ile Thr Ser Gly Thr Leu Val Pro Val Thr Lys Asn Asp
    220                 225                 230

Ile Val Lys Val Glu Gly Ile Asp Ser Thr Asp Gly Asn Asn Gln Pro
235                 240                 245                 250

Asn Thr Pro Asp Ile Ala Ala His Leu Trp Tyr Phe Gly Ser Met Ala
                255                 260                 265

Thr Cys Leu


<210> SEQ ID NO 5
<211> LENGTH: 1070
<212> TYPE: DNA
<213> ORGANISM: Thermomyces ibadanensis
<220> FEATURE:
<221> NAME/KEY: CDS
<222> LOCATION: (1)..(67)
<220> FEATURE:
<221> NAME/KEY: mat_peptide
<222> LOCATION: (67)..()
<220> FEATURE:
<221> NAME/KEY: CDS
<222> LOCATION: (128)..(296)
<220> FEATURE:
<221> NAME/KEY: CDS
<222> LOCATION: (357)..(690)
<220> FEATURE:
<221> NAME/KEY: CDS
<222> LOCATION: (765)..(1067)

<400> SEQUENCE: 5

atg cgg agc tcc ctc gtg ctg ttc ttc ctc tct gcg tgg acg gcc ttg       48
Met Arg Ser Ser Leu Val Leu Phe Phe Leu Ser Ala Trp Thr Ala Leu
        -20                 -15                 -10

gcg cgg cct gtt cga cga g gtatgtagca agggacacta ttacatgttg            97
Ala Arg Pro Val Arg Arg
    -5              -1

accttggtga ttctaagact gcatgcgcag cg  gtt ccg caa gat ctg ctc gac     150
                                 Ala Val Pro Gln Asp Leu Leu Asp
                                                 5

cag ttt gaa ctc ttt tca caa tat tcg gcg gcc gca tac tgt gcg gca      198
Gln Phe Glu Leu Phe Ser Gln Tyr Ser Ala Ala Ala Tyr Cys Ala Ala
    10                  15                  20

aac aat cat gct cca gtg ggc tca gac gta acg tgc tcg gag aat gtc      246
Asn Asn His Ala Pro Val Gly Ser Asp Val Thr Cys Ser Glu Asn Val
25                  30                  35                  40

tgc cct gag gta gat gcg gcg gac gca acg ttt ctc tat tct ttt gaa      294
Cys Pro Glu Val Asp Ala Ala Asp Ala Thr Phe Leu Tyr Ser Phe Glu
                45                  50                  55

ga  gtgggtgtcg acaaagcaca gagacagtag tagagacagc agtctaactg           346
Asp

agatgtgcag t tct gga tta ggc gat gtt acc ggc ctt ctc gct ctc gac     396
             Ser Gly Leu Gly Asp Val Thr Gly Leu Leu Ala Leu Asp
                     60                  65                  70
```

-continued

```
aac acg aat aaa ctg atc gtc ctc tct ttc cgc ggc tct cgc tca gta      444
Asn Thr Asn Lys Leu Ile Val Leu Ser Phe Arg Gly Ser Arg Ser Val
                75                  80                  85

gag aac tgg atc gcg aac ctc gcc gcc gac ctg aca gaa ata tct gac      492
Glu Asn Trp Ile Ala Asn Leu Ala Ala Asp Leu Thr Glu Ile Ser Asp
            90                  95                  100

atc tgc tcc ggc tgc gag ggg cat gtc ggc ttc gtt act tct tgg agg      540
Ile Cys Ser Gly Cys Glu Gly His Val Gly Phe Val Thr Ser Trp Arg
        105                 110                 115

tct gta gcc gac act ata agg gag cag gtg cag aat gcc gtg aac gag      588
Ser Val Ala Asp Thr Ile Arg Glu Gln Val Gln Asn Ala Val Asn Glu
    120                 125                 130

cat ccc gat tac cgc gtg gtc ttt acc gga cat agc ttg gga ggc gca      636
His Pro Asp Tyr Arg Val Val Phe Thr Gly His Ser Leu Gly Gly Ala
135                 140                 145                 150

ctg gca act att gcc gca gca gct ctg cga gga aat gga tac aat atc      684
Leu Ala Thr Ile Ala Ala Ala Ala Leu Arg Gly Asn Gly Tyr Asn Ile
                155                 160                 165

gac gtg gtatgtggga agaagccacc cagacaaaca attatgtgga aacatgcaag      740
Asp Val

gatggctaat acacggtcca acag ttc tca tat ggc gcg ccc cgc gtc ggt      791
                           Phe Ser Tyr Gly Ala Pro Arg Val Gly
                               170                 175

aac agg gca ttt gca gaa ttc ctg acc gca cag acg ggc ggc acc ctg      839
Asn Arg Ala Phe Ala Glu Phe Leu Thr Ala Gln Thr Gly Gly Thr Leu
        180                 185                 190

tat cgc atc acc cat acc aat gat atc gtc cct aga ctc cct cct cga      887
Tyr Arg Ile Thr His Thr Asn Asp Ile Val Pro Arg Leu Pro Pro Arg
    195                 200                 205

gac tgg ggt tac agc cac tct agc ccg gag tac tgg gtc acg tct ggt      935
Asp Trp Gly Tyr Ser His Ser Ser Pro Glu Tyr Trp Val Thr Ser Gly
210                 215                 220                 225

aac gac gtc cca gtg acc gca aac gac atc acc gtc gtg gag ggc atc      983
Asn Asp Val Pro Val Thr Ala Asn Asp Ile Thr Val Val Glu Gly Ile
                230                 235                 240

gat tcc acc gac ggg aac aac cag ggg aat atc cca gac atc cct tcg     1031
Asp Ser Thr Asp Gly Asn Asn Gln Gly Asn Ile Pro Asp Ile Pro Ser
            245                 250                 255

cat cta tgg tat ttc ggt ccc att tca gag tgt gat tag                 1070
His Leu Trp Tyr Phe Gly Pro Ile Ser Glu Cys Asp
        260                 265


<210> SEQ ID NO 6
<211> LENGTH: 291
<212> TYPE: PRT
<213> ORGANISM: Thermomyces ibadanensis

<400> SEQUENCE: 6

Met Arg Ser Ser Leu Val Leu Phe Phe Leu Ser Ala Trp Thr Ala Leu
        -20                 -15                 -10

Ala Arg Pro Val Arg Arg Ala Val Pro Gln Asp Leu Leu Asp Gln Phe
    -5              -1  1               5                   10

Glu Leu Phe Ser Gln Tyr Ser Ala Ala Ala Tyr Cys Ala Ala Asn Asn
                15                  20                  25

His Ala Pro Val Gly Ser Asp Val Thr Cys Ser Glu Asn Val Cys Pro
            30                  35                  40

Glu Val Asp Ala Ala Asp Ala Thr Phe Leu Tyr Ser Phe Glu Asp Ser
        45                  50                  55
```

-continued

```
Gly Leu Gly Asp Val Thr Gly Leu Leu Ala Leu Asp Asn Thr Asn Lys
    60                  65                  70

Leu Ile Val Leu Ser Phe Arg Gly Ser Arg Ser Val Glu Asn Trp Ile
75                  80                  85                  90

Ala Asn Leu Ala Ala Asp Leu Thr Glu Ile Ser Asp Ile Cys Ser Gly
                95                  100                 105

Cys Glu Gly His Val Gly Phe Val Thr Ser Trp Arg Ser Val Ala Asp
            110                 115                 120

Thr Ile Arg Glu Gln Val Gln Asn Ala Val Asn Glu His Pro Asp Tyr
        125                 130                 135

Arg Val Val Phe Thr Gly His Ser Leu Gly Gly Ala Leu Ala Thr Ile
    140                 145                 150

Ala Ala Ala Ala Leu Arg Gly Asn Gly Tyr Asn Ile Asp Val Phe Ser
155                 160                 165                 170

Tyr Gly Ala Pro Arg Val Gly Asn Arg Ala Phe Ala Glu Phe Leu Thr
                175                 180                 185

Ala Gln Thr Gly Gly Thr Leu Tyr Arg Ile Thr His Thr Asn Asp Ile
            190                 195                 200

Val Pro Arg Leu Pro Pro Arg Asp Trp Gly Tyr Ser His Ser Ser Pro
        205                 210                 215

Glu Tyr Trp Val Thr Ser Gly Asn Asp Val Pro Val Thr Ala Asn Asp
    220                 225                 230

Ile Thr Val Val Glu Gly Ile Asp Ser Thr Asp Gly Asn Asn Gln Gly
235                 240                 245                 250

Asn Ile Pro Asp Ile Pro Ser His Leu Trp Tyr Phe Gly Pro Ile Ser
                255                 260                 265

Glu Cys Asp


<210> SEQ ID NO 7
<211> LENGTH: 1064
<212> TYPE: DNA
<213> ORGANISM: Talaromyces emersonii
<220> FEATURE:
<221> NAME/KEY: CDS
<222> LOCATION: (1)..(88)
<220> FEATURE:
<221> NAME/KEY: mat_peptide
<222> LOCATION: (88)..()
<220> FEATURE:
<221> NAME/KEY: CDS
<222> LOCATION: (142)..(310)
<220> FEATURE:
<221> NAME/KEY: CDS
<222> LOCATION: (362)..(695)
<220> FEATURE:
<221> NAME/KEY: CDS
<222> LOCATION: (756)..(1061)

<400> SEQUENCE: 7

atg ttc aaa tcg gcc gct gtg cgg gcc att gct gcc ctc gga ctg act        48
Met Phe Lys Ser Ala Ala Val Arg Ala Ile Ala Ala Leu Gly Leu Thr
                -25                 -20                 -15

gcg tca gtc ttg gct gct cct gtt gaa ctg ggc cgt cga g gtaaggaagc       98
Ala Ser Val Leu Ala Ala Pro Val Glu Leu Gly Arg Arg
            -10                 -5              -1

atgacggaga gaacaccctg tgcgacctgc tgacatcctt cag at  gtt tct cag       152
                                                Asp Val Ser Gln

gac ctc ttc gac cag ctc aat ctt ttc gag cag tac tcg gcg gct gcg       200
Asp Leu Phe Asp Gln Leu Asn Leu Phe Glu Gln Tyr Ser Ala Ala Ala
5                   10                  15                  20
```

-continued

```
tac tgt tca gct aac aat gag gcc tct gcc ggc acg gca atc tct tgc      248
Tyr Cys Ser Ala Asn Asn Glu Ala Ser Ala Gly Thr Ala Ile Ser Cys
                25                  30                  35

tcc gca ggc aat tgc ccg ttg gtc cag cag gct gga gca acc atc ctg      296
Ser Ala Gly Asn Cys Pro Leu Val Gln Gln Ala Gly Ala Thr Ile Leu
            40                  45                  50

tat tca ttc aac aa  gtgggtgtca cggaaaagat tgttgatacc aacatgttga      350
Tyr Ser Phe Asn Asn
        55

cgtgttgtca g c att ggc tct ggc gat gtg acg ggt ttt ctc gct ctc       398
               Ile Gly Ser Gly Asp Val Thr Gly Phe Leu Ala Leu
                       60                  65

gac tcg acg aat caa ttg atc gtc ttg tca ttc cgg gga tca gag act      446
Asp Ser Thr Asn Gln Leu Ile Val Leu Ser Phe Arg Gly Ser Glu Thr
70                  75                  80                  85

ctc gaa aac tgg atc gct gac ctg gaa gct gac ctg gtc gat gcc tct      494
Leu Glu Asn Trp Ile Ala Asp Leu Glu Ala Asp Leu Val Asp Ala Ser
                90                  95                  100

gcc atc tgt tcc ggc tgt gaa gca cac gat ggg ttc ctt tca tcc tgg      542
Ala Ile Cys Ser Gly Cys Glu Ala His Asp Gly Phe Leu Ser Ser Trp
            105                 110                 115

aat tca gtc gcc agc act ctg aca tcc aaa atc tcg tcg gcc gtc aac      590
Asn Ser Val Ala Ser Thr Leu Thr Ser Lys Ile Ser Ser Ala Val Asn
        120                 125                 130

gaa cat ccc agc tac aag ctg gtc ttc acc ggc cac agt ctc gga gcc      638
Glu His Pro Ser Tyr Lys Leu Val Phe Thr Gly His Ser Leu Gly Ala
    135                 140                 145

gcc ttg gct aca ctt gga gcc gtt tct ctt aga gag agc gga tat aat      686
Ala Leu Ala Thr Leu Gly Ala Val Ser Leu Arg Glu Ser Gly Tyr Asn
150                 155                 160                 165

att gac ctc gtaagtttcc ggcacgggcg tcgtcatcat cgagcggaaa              735
Ile Asp Leu

gactgaccgg ttaactgcag tac aat tat ggc tgc ccc cgg gtc ggt aac acc    788
                      Tyr Asn Tyr Gly Cys Pro Arg Val Gly Asn Thr
                          170                 175

gcg ctc gca gac ttc atc acc acg caa tcc gga ggc aca aat tac cgc      836
Ala Leu Ala Asp Phe Ile Thr Thr Gln Ser Gly Gly Thr Asn Tyr Arg
180                 185                 190                 195

gtc acg cat tcc gat gac cct gtc ccc aag ctg cct ccc agg agt ttt      884
Val Thr His Ser Asp Asp Pro Val Pro Lys Leu Pro Pro Arg Ser Phe
                200                 205                 210

gga tac agc caa ccg agc cca gag tac tgg atc acc tca ggg aac aat      932
Gly Tyr Ser Gln Pro Ser Pro Glu Tyr Trp Ile Thr Ser Gly Asn Asn
            215                 220                 225

gta act gtt caa ccg tcc gac atc gag gtc atc gaa ggc gtc gac tcc      980
Val Thr Val Gln Pro Ser Asp Ile Glu Val Ile Glu Gly Val Asp Ser
        230                 235                 240

act gca ggc aac gac ggc acc cct gct ggc ctt gac att gat gct cat     1028
Thr Ala Gly Asn Asp Gly Thr Pro Ala Gly Leu Asp Ile Asp Ala His
    245                 250                 255

cgg tgg tac ttt gga ccc att agc gca tgt tcg tga                     1064
Arg Trp Tyr Phe Gly Pro Ile Ser Ala Cys Ser
260                 265                 270
```

<210> SEQ ID NO 8
<211> LENGTH: 299
<212> TYPE: PRT
<213> ORGANISM: Talaromyces emersonii -continued

<400> SEQUENCE: 8

```
Met Phe Lys Ser Ala Ala Val Arg Ala Ile Ala Ala Leu Gly Leu Thr
                -25                 -20                 -15

Ala Ser Val Leu Ala Ala Pro Val Glu Leu Gly Arg Arg Asp Val Ser
            -10                 -5              -1  1

Gln Asp Leu Phe Asp Gln Leu Asn Leu Phe Glu Gln Tyr Ser Ala Ala
    5                   10                  15

Ala Tyr Cys Ser Ala Asn Asn Glu Ala Ser Ala Gly Thr Ala Ile Ser
20                  25                  30                  35

Cys Ser Ala Gly Asn Cys Pro Leu Val Gln Gln Ala Gly Ala Thr Ile
                40                  45                  50

Leu Tyr Ser Phe Asn Asn Ile Gly Ser Gly Asp Val Thr Gly Phe Leu
            55                  60                  65

Ala Leu Asp Ser Thr Asn Gln Leu Ile Val Leu Ser Phe Arg Gly Ser
        70                  75                  80

Glu Thr Leu Glu Asn Trp Ile Ala Asp Leu Glu Ala Asp Leu Val Asp
    85                  90                  95

Ala Ser Ala Ile Cys Ser Gly Cys Glu Ala His Asp Gly Phe Leu Ser
100                 105                 110                 115

Ser Trp Asn Ser Val Ala Ser Thr Leu Thr Ser Lys Ile Ser Ser Ala
                120                 125                 130

Val Asn Glu His Pro Ser Tyr Lys Leu Val Phe Thr Gly His Ser Leu
            135                 140                 145

Gly Ala Ala Leu Ala Thr Leu Gly Ala Val Ser Leu Arg Glu Ser Gly
        150                 155                 160

Tyr Asn Ile Asp Leu Tyr Asn Tyr Gly Cys Pro Arg Val Gly Asn Thr
    165                 170                 175

Ala Leu Ala Asp Phe Ile Thr Thr Gln Ser Gly Gly Thr Asn Tyr Arg
180                 185                 190                 195

Val Thr His Ser Asp Asp Pro Val Pro Lys Leu Pro Pro Arg Ser Phe
                200                 205                 210

Gly Tyr Ser Gln Pro Ser Pro Glu Tyr Trp Ile Thr Ser Gly Asn Asn
            215                 220                 225

Val Thr Val Gln Pro Ser Asp Ile Glu Val Ile Glu Gly Val Asp Ser
        230                 235                 240

Thr Ala Gly Asn Asp Gly Thr Pro Ala Gly Leu Asp Ile Asp Ala His
    245                 250                 255

Arg Trp Tyr Phe Gly Pro Ile Ser Ala Cys Ser
260                 265                 270
```

<210> SEQ ID NO 9
<211> LENGTH: 1074
<212> TYPE: DNA
<213> ORGANISM: Talaromyces byssochlamydoides
<220> FEATURE:
<221> NAME/KEY: CDS
<222> LOCATION: (1)..(85)
<220> FEATURE:
<221> NAME/KEY: mat_peptide
<222> LOCATION: (85)..()
<220> FEATURE:
<221> NAME/KEY: CDS
<222> LOCATION: (150)..(318)
<220> FEATURE:
<221> NAME/KEY: CDS
<222> LOCATION: (376)..(709)
<220> FEATURE:
<221> NAME/KEY: CDS
<222> LOCATION: (760)..(1071)

-continued

```
<400> SEQUENCE: 9

atg ttc aaa tca act gtc cgg gcc atc gcc gcc ctc gga ctg acc tcg       48
Met Phe Lys Ser Thr Val Arg Ala Ile Ala Ala Leu Gly Leu Thr Ser
            -25                 -20                 -15

tca gtc ttt gct gct cct atc gaa ctg ggc cgt cga g gtaaggggca          95
Ser Val Phe Ala Ala Pro Ile Glu Leu Gly Arg Arg
        -10                 -5                  -1

tgaaaactcc ctgtatggca tctcatctgg cagcatatct actgacatcc tcag at       151
                                                            Asp

gtt tcg gag cag ctc ttc aac cag ttc aat ctc ttc gag cag tat tcc      199
Val Ser Glu Gln Leu Phe Asn Gln Phe Asn Leu Phe Glu Gln Tyr Ser
            5                   10                  15

gcg gct gcg tac tgt cca gcc aac ttt gag tcc gct tcc ggc gcg gca      247
Ala Ala Ala Tyr Cys Pro Ala Asn Phe Glu Ser Ala Ser Gly Ala Ala
        20                  25                  30

att tct tgt tcc aca ggc aat tgc ccg ctc gtc caa cag gct ggc gca      295
Ile Ser Cys Ser Thr Gly Asn Cys Pro Leu Val Gln Gln Ala Gly Ala
    35                  40                  45

acc acc ctg tat gca ttc aac aa  gtgagtgtca tggaaaggct tgttggtaca     348
Thr Thr Leu Tyr Ala Phe Asn Asn
50                  55

ccgtacgggt atgttgactg tcatcag c atc ggc tct ggc gat gtg acg ggt      400
                                Ile Gly Ser Gly Asp Val Thr Gly
                                        60                  65

ttt ctt gct gtc gat ccg acc aac cga ctc atc gtc ttg tcg ttc cgg      448
Phe Leu Ala Val Asp Pro Thr Asn Arg Leu Ile Val Leu Ser Phe Arg
                70                  75                  80

ggg tca gag agt ctc gag aac tgg atc act aat ctc agc gcc gac ctg      496
Gly Ser Glu Ser Leu Glu Asn Trp Ile Thr Asn Leu Ser Ala Asp Leu
            85                  90                  95

gtc gat gcc tct gca atc tgt tcc ggg tgt gaa gcc cat gac gga ttc      544
Val Asp Ala Ser Ala Ile Cys Ser Gly Cys Glu Ala His Asp Gly Phe
        100                 105                 110

tat tcg tct tgg caa tca gtt gcc agc act ctg acc tcc caa atc tcg      592
Tyr Ser Ser Trp Gln Ser Val Ala Ser Thr Leu Thr Ser Gln Ile Ser
    115                 120                 125

tcg gcc ctc tcg gca tat cca aac tac aag ctg gtc ttc acc ggc cac      640
Ser Ala Leu Ser Ala Tyr Pro Asn Tyr Lys Leu Val Phe Thr Gly His
130                 135                 140                 145

agt ctc gga gcc gcc tta gct aca ctt gga gct gtc tct ctc agg gag      688
Ser Leu Gly Ala Ala Leu Ala Thr Leu Gly Ala Val Ser Leu Arg Glu
                150                 155                 160

agt gga tac aat atc gac ctc gtaagttcct ggcattgcca tcatggaaag         739
Ser Gly Tyr Asn Ile Asp Leu
            165

agactcacag ttaactgtag tac aac ttt ggc tgt ccc cgg gtc ggc aac act    792
                      Tyr Asn Phe Gly Cys Pro Arg Val Gly Asn Thr
                          170                 175

gcg ctc gca gac ttt att acc aac caa acc ggt ggc aca aat tac cgg      840
Ala Leu Ala Asp Phe Ile Thr Asn Gln Thr Gly Gly Thr Asn Tyr Arg
180                 185                 190                 195

gta acg cat tac gag gac cct gtc ccc aag ctg cct ccc agg agt ttt      888
Val Thr His Tyr Glu Asp Pro Val Pro Lys Leu Pro Pro Arg Ser Phe
                200                 205                 210

gga tac agc caa cct agc ccg gaa tac tgg atc acg tcg gga aac aat      936
Gly Tyr Ser Gln Pro Ser Pro Glu Tyr Trp Ile Thr Ser Gly Asn Asn
            215                 220                 225
```

-continued

```
gtg act gtg act tcg tcc gac atc gat gtc gtc gtg ggt gtc gac tcg      984
Val Thr Val Thr Ser Ser Asp Ile Asp Val Val Val Gly Val Asp Ser
        230                 235                 240

act gca ggc aac gac ggg acg cct gat ggc ctt gac act gct gcc cat     1032
Thr Ala Gly Asn Asp Gly Thr Pro Asp Gly Leu Asp Thr Ala Ala His
    245                 250                 255

agg tgg tat ttt gga cct act acc gaa tgt tcg tcg tca tga             1074
Arg Trp Tyr Phe Gly Pro Thr Thr Glu Cys Ser Ser Ser
260                 265                 270


<210> SEQ ID NO 10
<211> LENGTH: 300
<212> TYPE: PRT
<213> ORGANISM: Talaromyces byssochlamydoides

<400> SEQUENCE: 10

Met Phe Lys Ser Thr Val Arg Ala Ile Ala Ala Leu Gly Leu Thr Ser
            -25                 -20                 -15

Ser Val Phe Ala Ala Pro Ile Glu Leu Gly Arg Arg Asp Val Ser Glu
        -10                 -5              -1  1

Gln Leu Phe Asn Gln Phe Asn Leu Phe Glu Gln Tyr Ser Ala Ala Ala
5                   10                  15                  20

Tyr Cys Pro Ala Asn Phe Glu Ser Ala Ser Gly Ala Ala Ile Ser Cys
                25                  30                  35

Ser Thr Gly Asn Cys Pro Leu Val Gln Gln Ala Gly Ala Thr Thr Leu
            40                  45                  50

Tyr Ala Phe Asn Asn Ile Gly Ser Gly Asp Val Thr Gly Phe Leu Ala
        55                  60                  65

Val Asp Pro Thr Asn Arg Leu Ile Val Leu Ser Phe Arg Gly Ser Glu
    70                  75                  80

Ser Leu Glu Asn Trp Ile Thr Asn Leu Ser Ala Asp Leu Val Asp Ala
85                  90                  95                  100

Ser Ala Ile Cys Ser Gly Cys Glu Ala His Asp Gly Phe Tyr Ser Ser
                105                 110                 115

Trp Gln Ser Val Ala Ser Thr Leu Thr Ser Gln Ile Ser Ser Ala Leu
            120                 125                 130

Ser Ala Tyr Pro Asn Tyr Lys Leu Val Phe Thr Gly His Ser Leu Gly
        135                 140                 145

Ala Ala Leu Ala Thr Leu Gly Ala Val Ser Leu Arg Glu Ser Gly Tyr
    150                 155                 160

Asn Ile Asp Leu Tyr Asn Phe Gly Cys Pro Arg Val Gly Asn Thr Ala
165                 170                 175                 180

Leu Ala Asp Phe Ile Thr Asn Gln Thr Gly Gly Thr Asn Tyr Arg Val
                185                 190                 195

Thr His Tyr Glu Asp Pro Val Pro Lys Leu Pro Pro Arg Ser Phe Gly
            200                 205                 210

Tyr Ser Gln Pro Ser Pro Glu Tyr Trp Ile Thr Ser Gly Asn Asn Val
        215                 220                 225

Thr Val Thr Ser Ser Asp Ile Asp Val Val Val Gly Val Asp Ser Thr
    230                 235                 240

Ala Gly Asn Asp Gly Thr Pro Asp Gly Leu Asp Thr Ala Ala His Arg
245                 250                 255                 260

Trp Tyr Phe Gly Pro Thr Thr Glu Cys Ser Ser Ser
                265                 270
```

-continued

```
<210> SEQ ID NO 11
<211> LENGTH: 24
<212> TYPE: DNA
<213> ORGANISM: Artificial Sequence
<220> FEATURE:
<223> OTHER INFORMATION: Oligo 19671

<400> SEQUENCE: 11

ctcccttctc tgaacaataa accc                                          24


<210> SEQ ID NO 12
<211> LENGTH: 77
<212> TYPE: DNA
<213> ORGANISM: Artificial Sequence
<220> FEATURE:
<223> OTHER INFORMATION: Oligo 991222J1
<220> FEATURE:
<221> NAME/KEY: misc_feature
<222> LOCATION: (50)..(57)
<223> OTHER INFORMATION: n is C or G or T or A

<400> SEQUENCE: 12

cctctagatc tcgagctcgg tcaccggtgg cctccgcggc cgctgctawn nwnnwnnaag   60

acatgtccca attaacc                                                  77
```

LIPASE VARIANTS

CROSS-REFERENCE TO RELATED APPLICATIONS

This application is a 35 U.S.C. 371 national application of PCT/DK02/00084 filed 7 Feb. 2002 (the international application was published under PCT Article 21(2) in English), which claims priority or the benefit under 35 U.S.C. 119 of Danish application No. PA 2001 00195 filed 7 Feb. 2001 and U.S. provisional application No. 60/269,140, filed Feb. 15, 2001, the contents of which are fully incorporated herein by reference.

FIELD OF THE INVENTION

The present invention relates to lipase variants with reduced potential for odor generation and to a method of preparing them. It particularly relates to variants suited for use in detergent compositions, more particularly variants of the *Thermomyces lanuginosus* lipase showing a first-wash effect and a reduced tendency to form odors when washing cloth soiled with milk fat.

BACKGROUND OF THE INVENTION

Lipases are useful, e.g., as detergent enzymes to remove lipid or fatty stains from clothes and other textiles, as additives to dough for bread and other baked products. Thus, a lipase derived from *Thermomyces lanuginosus* (synonym *Humicola lanuginosa*, EP 258 068 and EP 305 216) is sold for detergent use under the tradename Lipolase® (product of Novo Nordisk A/S). WO 0060063 describes variants of the *T. lanuginosus* lipase with a particularly good first-wash performance in a detergent solution. WO 9704079, WO 9707202 and WO 0032758 also disclose variants of the *T. lanuginosus* lipase.

In some applications, it is of interest to minimize the formation of odor-generating short-chain fatty acids. Thus, it is known that laundry detergents with lipases may sometimes leave residual odors attached to cloth soiled with milk (EP 430315).

SUMMARY OF THE INVENTION

The inventors have found that attaching a peptide extension to the C-terminal amino acid of a lipase may reduce the tendency to form odor. This may lead to lipase variants with a reduced odor generation when washing textile soiled with fat which includes relatively short-chain fatty acyl groups (e.g. up to $C_8$) such as dairy stains containing butter fat or tropical oils such as coconut oil or palm kernel oil. The variants may have an increased specificity for long-chain acyl groups over the short-chain acyl and/or an increased activity ratio at alkaline pH to neutral pH, i.e. a relatively low lipase activity at the neutral pH (around pH 7) during rinsing compared to the lipase activity at alkaline pH (e.g. pH 9 or 10) similar to the pH in a detergent solution.

Accordingly, the invention provides a method of producing a lipase by attaching a peptide extension to the C-terminal of a parent lipase and screening resulting polypeptides for lipases with any of the above improved properties.

The invention also provides a polypeptide having lipase activity and having an amino acid sequence which comprises a parent polypeptide with lipase activity and a peptide extension attached to the C-terminal of the parent polypeptide.

The invention further provides a detergent composition and a method of preparing a detergent using a lipase with the above properties.

DETAILED DESCRIPTION OF THE INVENTION

Parent Lipase

The parent lipase may be a fungal lipase with an amino acid sequence having at least 50% identity to the sequence of the *T. lanuginosus* lipase shown in SEQ ID NO: 2.

Thus, the parent lipase may be derived from a strain of *Talaromyces* or *Thermomyces*, particularly *Talaromyces thermophilus, Thermomyces ibadanensis, Talaromyces emersonii* or *Talaromyces byssochlamydoides*, using probes designed on the basis of the DNA sequences in this specification.

More particularly, the parent lipase may be a lipase isolated from the organisms indicated below and having the indicated amino acid sequence. Strains of *Escherichia coli* containing the genes were deposited under the terms of the Budapest Treaty with the DSMZ as follows:

| Source organism | Gene and polypeptide sequences | Clone deposit No. | Date deposited |
|---|---|---|---|
| *Thermomyces lanuginosus* sus DSM 4109 | SEQ ID NO: 1 and 2 | | |
| *Talaromyces thermophilus* ATCC 10518 | SEQ ID NO: 3 and 4 | DSM 14051 | Feb. 8, 2001 |
| *Thermomyces ibadanensis* CBS 281.67 | SEQ ID NO: 5 and 6 | DSM 14049 | Feb. 8, 2001 |
| *Talaromyces emersonii* UAMH 5005 | SEQ ID NO: 7 and 8 | DSM 14048 | Feb. 8, 2001 |
| *Talaromyces byssochlamydoides* CBS 413.71 | SEQ ID NO: 9 and 10 | DSM 14047 | Feb. 8, 2001 |

The above source organisms are freely available on commercial terms. The strain collections are at the following addresses:

DSMZ (Deutsche Sammlung von Microorganismen und Zellkulturen GmbH), Mascheroder Weg 1b, D-38124 Braunschweig DE ATCC (American Type Culture Collection), 10801 University Boulevard, Manassas, Va. 20110-2209, USA.

CBS (Centraalbureau voor Schimmelcultures), Uppsalalaan 8, 3584 CT Utrecht, The Netherlands.

UAMH (University of Alberta Mold Herbarium & Culture Collection), Devonian Botanic Garden, Edmonton, Alberta, Canada T6G 3GI.

Alternatively, the parent lipase may be a variant obtained by altering the amino acid sequence of any of the above lipases, particularly a variant having first-wash activity as described in WO 0060063 or as described below.

Peptide Extension at C-terminal

The invention provides attachment of a peptide addition by a peptide bond to the C-terminal amino acid of a parent lipase (e.g. to L269 of the *T. lanuginosus* lipase shown as SEQ ID NO: 2). The peptide extension may be attached by site-directed or random mutagenesis.

The peptide extension at the C-terminal may consist of 2–15 amino acid residues, particularly 2–11 or 3–10, e.g. 2, 3, 4, 5, 7, 9 or 11 residues.

The extension may particularly have the following residues at the positions indicated (counting from the original C-terminal):

- a negative amino acid residue (e.g. D or E) at the first position,
- a small, electrically uncharged amino acid (e.g. S, T, V or L) at the $2^{nd}$ and/or the $3^{rd}$ position, and/or
- a positive amino acid residue (e.g. H or K) at the $3^{rd}$–$7^{th}$ position, particularly the $4^{th}$, $5^{th}$ or $6^{th}$.

The peptide extension may be HTPSSGRGGHR (SEQ ID NO: 13) or a truncated form thereof, e.g. HTPSSGRGG (SEQ ID NO: 13), HTPSSGR (SEQ ID NO: 13), HTPSS (SEQ ID NO: 13) or HTP. Other examples are KV, EST, LVY, RHT, SVF, SVT, TAD, TPA, AGVF (SEQ ID NO: 14) and PGLPFKRV (SEQ ID NO: 15).

The peptide extension may be attached by mutagenesis using a vector (a plasmid) encoding the parent polypeptide and an oligonucleotide having a stop codon corresponding to an extension of 2–15 amino acids from the C-terminal. The nucleotides between the C-terminal and the stop codon may be random or may be biased to favor the amino acids described above. One way of doing this would be to design a DNA oligo, which contains the desired random mutations as well has the sequence necessary to hybridize to the 3 end of the gene of interest. This DNA oligo is used in a PCR reaction along with an oligo with the capability of hybridizing to the opposite DNA strand (as known to a person skilled in the art). The PCR fragment is then cloned into the desired context (expression vector).

Increased Long-chain/Short-chain Specificity

The lipase of the invention may have an increased long-chain/short-chain specificity compared to the parent enzyme, e.g. an increased ratio of activity on long-chain (e.g. $C_{16}$–$C_{20}$) triglycerides to the activity on short-chain (e.g. $C_4$–$C_8$) triglycerides. This may be determined as the ratio of SLU with olive oil as the substrate and LU with tributyrin as substrate (methods described later in this specification).

Increased Alkaline/Neutral Activity Ratio

The lipase of the invention may have an increased alkaline/neutral activity ratio compared to the parent enzyme, i.e. an increased ratio of lipase activity (e.g. lipase activity) at alkaline pH (e.g. pH 9–10) to the activity at neutral pH (around pH 7). This may be determined with tributyrine as the substrate as described later in this specification.

Substitution with Positive Amino Acid

The parent lipase may comprise one or more (e.g. 2–4, particularly two) substitutions of an electrically neutral or negatively charged amino acid with a positively charged amino acid near a position corresponding to E1 or Q249 of SEQ ID NO: 2. The positively charged amino acid may be K, R or H, particularly R. The negative or neutral amino acid may be any other amino acid, The substitution is at the surface of the three-dimensional structure within 15 Å of E1 or Q249 of SEQ ID NO: 2, e.g. at a position corresponding to any of 1–11, 90, 95, 169, 171–175, 192–211, 213–226, 228–258 or 260–262.

The substitution may be within 10 Å of E1 or Q249, e.g. corresponding to any of positions 1–7, 10, 175, 195, 197–202, 204–206, 209, 215, 219–224, 230–239, 242–254.

The substitution may be within 15 Å of E1, e.g. corresponding to any of positions 1–11, 169, 171, 192–199, 217–225, 228–240, 243–247, 249, 261–262.

The substitution is most preferably within 10 Å of E1, e.g. corresponding to any of positions 1–7, 10, 219–224 and 230–239.

Thus, some particular substitutions are those corresponding to S3R, S224R, P229R, T231R, N233R, D234R and T244R.

Amino Acids at Positions 90–101 and 210

The parent lipase may particularly meet certain limitations on electrically charged amino acids at positions corresponding to 90–101 and 210. Lipases meeting the charge limitations are particularly effective in a detergent with high content of anionic.

Thus, amino acid 210 may be negative. E210 may be unchanged or it may have the substitution E210D/C/Y, particularly E210D.

The lipase may comprise a negatively charged amino acid at any of positions 90–101 (particularly 94–101), e.g. at position D96 and/or E99.

Further, the lipase may comprise a neutral or negative amino acid at position N94, i.e. N94(neutral or negative), e.g. N94N/D/E.

Also, the lipase may have a negative or neutral net electric charge in the region 90–101 (particularly 94–101), i.e. the number of negative amino acids may be equal to or greater than the number of positive amino acids. Thus, the region may be unchanged from Lipolase, having two negative amino acids (D96 and E99) and one positive (K98), and having a neutral amino acid at position 94 (N94), or the region may be modified by one or more substitutions.

Alternatively, two of the three amino acids N94, N96 and E99 may have a negative or unchanged electric charge. Thus, all three amino acids may be unchanged or may be changed by a conservative or negative substitution, i.e. N94(neutral or negative), D(negative) and E99(negative). Examples are N94D/E and D96E.

Further, one of the three amino acids N94, N96 and E99 may be substituted so as to increase the electric charge, i.e. N94(positive), D96(neutral or positive) or E99 (neutral or positive). Examples are N94K/R, D96I/L/N/S/W or E99N/Q/K/R/H.

The parent lipase may comprise a substitution corresponding to E99K combined with a negative amino acid in the region corresponding to 90–101, e.g. D96D/E.

The substitution of a neutral with a negative amino acid (N94D/E), may improve the performance in an anionic detergent. The substitution of a neutral amino acid with a positive amino acid (N94K/R) may provide a variant lipase with good performance both in an anionic detergent and in an anionic/non-ionic detergent (a detergent with e.g. 40–70% anionic out of total surfactant).

Amino Acids at other Positions

The parent lipase may optionally comprise substitution of other amino acids, particularly less than 10 or less than 5 such substitutions. Examples are substitutions corresponding to Q249R/K/H, R209P/S and G91A in SEQ ID NO: 2. Further substitutions may, e.g., be made according to principles known in the art, e.g. substitutions described in WO 92/05249, WO 94/25577, WO 95/22615, WO 97/04079 and WO 97/07202.

Parent Lipase Variants

The parent lipase may comprise substitutions corresponding to G91G/A+E99E/D/R/K+T231T/S/R/K+N233N/Q/R/K+Q249Q/N/R/K in SEQ ID NO: 2. Some particular examples are variants with substitutions corresponding to the following.

| |
|---|
| T231R + N233R |
| D96L + T231R + N233R |
| G91A + E99K + T231R + N233R + Q249R |
| R209P + T231R + N233R |
| E87K + G91D + D96L + G225P + T231R + N233R + Q249R + N251D |
| G91A + E99K + T189G + T231R + N233R + Q249R |
| D102G + T231R + N233R + Q249R |
| N33Q + N94K + D96L + T231R + N233R + Q249R |
| N33Q + D96S + T231R + N233R + Q249R |
| N33Q + D96S + V228I + T231R + N233R + Q249R |
| D62A + S83T + G91A + E99K + T231R + N233R + Q249R |
| E99N + N101S + T231R + N233R + Q249R |
| R84W + G91A + E99K + T231R + N233R + Q249R |
| V60G + D62E + G91A + E99K + T231R + N233R + Q249R |
| E99K + T231R + N233R + Q249R |
| T231R + N231R + Q249R |

Nomenclature for Amino Acid Modifications

The nomenclature used herein for defining mutations is essentially as described in WO 92/05249. Thus, T231R indicates a substitution of T in position 231 with R.

270PGLPFKRV indicates a peptide extension attached to the C-terminal (L269) of SEQ ID NO: 2.

Amino Acid Grouping

In this specification, amino acids are classified as negatively charged, positively charged or electrically neutral according to their electric charge at pH 10, which is typical of detergents. Thus, negative amino acids are E, D, C (cysteine) and Y, particularly E and D. Positive amino acids are R, K and H, particularly R and K. Neutral amino acids are G, A, V, L, I, P, F, W, S, T, M, N, Q and C when forming part of a disulfide bridge. A substitution with another amino acid in the same group (negative, positive or neutral) is termed a conservative substitution.

The neutral amino acids may be divided into hydrophobic or non-polar (G, A, V, L, I, P, F, W and C as part of a disulfide bridge) and hydrophilic or polar (S, T, M, N, Q).

Amino Acid Identity

The parent lipase has an amino acid identity of at least 50% with the *T. lanuginosus* lipase (SEQ ID NO: 2), particularly at least 55%, at least 60%, at least 75%, at least 85%, at least 90%, more than 95% or more than 98%.

The degree of identity may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–45), using GAP with the following settings for polypeptide sequence comparison: GAP creation penalty of 3.0 and GAP extension penalty of 0.1.

Amino Acid Sequence Alignment

In this specification, amino acid residues are identified by reference to SEQ ID NO: 2. To find corresponding positions in another lipase sequence, the sequence is aligned to SEQ ID NO: 2 by using the GAP alignment. GAP is provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–45). The following settings are used for polypeptide sequence comparison: GAP creation penalty of 3.0 and GAP extension penalty of 0.1.

DNA Sequence, Expression Vector, Host Cell, Production of Lipase

The invention provides a DNA sequence encoding the lipase of the invention, an expression vector harboring the DNA sequence, and a transformed host cell containing the DNA sequence or the expression vector. These may be obtained by methods known in the art.

The invention also provides a method of producing the lipase by culturing the transformed host cell under conditions conducive for the production of the lipase and recovering the lipase from the resulting broth. The method may be practiced according to principles known in the art.

Lipase Activity

Lipase Activity on Tributyrin at Neutral and Alkaline pH (LU7 and LU9)

A substrate for lipase is prepared by emulsifying tributyrin (glycerin tributyrate) using gum Arabic as emulsifier. The hydrolysis of tributyrin at 30° C. at pH 7 or 9 is followed in a pH-stat titration experiment. One unit of lipase activity (1 LU7 or 1 LU9) equals the amount of enzyme capable of releasing 1 μmol butyric acid/min at pH 7 or 9. LU7 is also referred to as LU.

The relative lipase activity at neutral and alkaline pH may be expressed as LU9/LU7. This ratio may be at least 2.0.

Lipase Activity on Triolein (SLU)

The lipase activity is measured at 30° C. and pH 9 with a stabilized olive oil emulsion (Sigma catalog No. 800-1) as the substrate, in a 5 mM Tris buffer containing 40 mM NaCl and 5 mM calcium chloride. 2.5 ml of the substrate is mixed with 12.5 ml buffer, the pH is adjusted to 9, 0.5 ml of diluted lipase sample is added, and the amount of oleic acid formed is followed by titration with a pH stat.

One SLU is the amount of lipase which liberates 1 μmole of titratable oleic acid per minute under these conditions.

The lipase may particularly have an activity of at least 4000 or at least 5000 SLU/mg enzyme protein.

The relative activity towards long-chain and short-chain acyl bonds in triglycerides at alkaline pH may be expressed as the ratio of SLU to LU9. SLU/LU9 may be at least 2.0, at least 3.0 or at least 4.0.

First-wash Performance

The first-wash performance of a lipase is determined as follows:

Style 400 cotton is cleaned by deionized water at 95° C. and is cut in swatches of 9×9 cm. 50 μl of lard/Sudan red (0.75 mg dye/g of lard) is applied to the center of each swatch, and the soiled swatches are heat treated at 70° C. for 25 minutes and cured overnight. 7 soiled swatches are washed for 20 minutes at 30° C. in a Terg-O-Tometer test washing machine in 1000 ml of wash liquor with 4 g/L of test detergent in water with hardness of 15° dH ($Ca^{2+}/Mg^{2+}$ 4:1), followed by 15 minutes rinsing in tap water and drying overnight.

The lipase is added to the wash liquor at a dosage of 0.25 mg enzyme protein per liter. A control is made without addition of lipase variant.

The soil removal is evaluated by measuring the remission at 460 nm after the first washing cycle, and the results are expressed as ΔR by subtracting the remission of a blank washed at the same conditions without lipase.

Test Detergent

The test detergent used in this specification has the following composition (in % by weight):

| | |
|---|---|
| Linear alkylbenzenesulfonate, $C_{10}$–$C_{13}$ | 12.6 |
| Alkyl sulfate, $C_{16}$–$C_{18}$ | 3.2 |
| Fatty acids, $C_{16}$–$C_{18,\ 18:2}$ | 0.9 |
| Alcohol ethoxylate, $C_{12}$–$C_{18}$, 6.7 EO | 13.2 |
| Zeolite | 35.2 |
| Sodium carbonate | 1.2 |
| Sodium hydrogencarbonate | 1.3 |
| Sodium silicate | 4.8 |
| Sodium sulfate | 1.9 |
| Sodium tetraborate | 2.7 |
| Phosphonate [1-hydroxyethane-1,2-diylbis(phosphonic acid)] | 0.1 |
| Sodium perborate monohydrate | 11.2 |
| Tetraacetylethylenediamine (TAED) | 6.3 |
| Copoly(acrylic acid/maleic acid) | 4.3 |
| SRP (soil release polymer) | 1.2 |

Detergent Additive

According to the invention, the lipase may typically be used as an additive in a detergent composition. This additive is conveniently formulated as a non-dusting granulate, a stabilized liquid, a slurry or a protected enzyme. The additive may be prepared by methods known in the art.

Detergent Composition

The detergent compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The detergent composition of the invention comprises the lipase of the invention and a surfactant. Additionally, it may optionally comprise a builder, another enzyme, a suds suppresser, a softening agent, a dye-transfer inhibiting agent and other components conventionally used in detergents such as soil-suspending agents, soil-releasing agents, optical brighteners, abrasives, bactericides, tarnish inhibitors, coloring agents, and/or encapsulated or non-encapsulated perfumes.

The detergent composition according to the invention can be in liquid, paste, gel, bar, tablet or granular forms. The pH (measured in aqueous solution at use concentration) will usually be neutral or alkaline, e.g. in the range of 7–11, particularly 9–11. Granular compositions according to the present invention can also be in "compact form", i.e. they may have a relatively higher density than conventional granular detergents, i.e. form 550 to 950 g/l.

The lipase of the invention, or optionally another enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

The detergent composition of the invention may comprise the lipase in an amount corresponding to 1–5,000 LU per gram of detergent, preferably 2–500 LU/g, e.g. 10–100 LU/g. The detergent may be dissolved in water to produce a wash liquor containing lipase in an amount corresponding to 2.5–1,500 LU per liter of wash liquor, particularly 10–500 LU/I, e.g. 30–200 LU/I. The amount of lipase protein may be 0.001–10 mg per gram of detergent or 0.001–100 mg per liter of wash liquor.

The surfactant system may comprise nonionic, anionic, cationic, ampholytic, and/or zwitterionic surfactants. As described above, the lipase variants of the invention are particularly suited for detergents comprising a combination of anionic and nonionic surfactant with 70–100% by weight of anionic surfactant and 0–30% by weight of nonionic, particularly 80–100% of anionic surfactant and 0–20% nonionic. As further described, some preferred lipases of the invention are also suited for detergents comprising 40–70% anionic and 30–60% non-ionic surfactant. The surfactant is typically present at a level from 0.1% to 60% by weight, e.g. 1% to 40%, particularly 10–40%. preferably from about 3% to about 20% by weight. Some examples of surfactants are described below.

Examples of anionic surfactants are alkyl sulfate, alkyl ethoxy sulfate, linear alkyl benzene sulfonate, alkyl alkoxylated sulfates.

Examples of anionic surfactants are polyalkylene oxide (e.g. polyethylene oxide) condensates of alkyl phenols, condensation products of primary and secondary aliphatic alcohols with ethylene oxide. polyethylene oxide condensates of alkyl phenols, condensation products of primary and secondary aliphatic alcohols, alkylpolysaccharides,and alkyl phenol ethoxylates and alcohol ethoxylates.

More specifically, the lipase of the invention may be incorporated in the detergent compositions described in WO 97/04079, WO 97/07202, WO 97/41212, WO 98/08939 and WO 97/43375.

EXAMPLES

Example 1

Preparation of Lipase Variants Using C-terminal Library

Creating the Library:

The purpose was to add 3 extra amino acids to the C-terminal. Additional amino acids on the C-terminal could increase the activity towards long chained triglycerides as compared to short-chained triglycerides, as well as impede activity at pH7 as compared to activity at pH10, and thus diminish the smell attributed to the lipase in the detergent, during and after wash.

A plasmid pENi1576 was constructed with a gene encoding a lipase having the amino acid sequence shown in SEQ ID NO: 2 with the substitutions G91A+E99K+T231R+N233R+Q249R.

A PCR reaction was made using oligo 19671 and 991222j1 (SEQ ID NO: 11 and 12) with pENi1576 as template in a total of 100 μl using PWO polymerase (Boehringer Mannheim). Oligo 991222J1 adds 3 extra amino acids on the C-terminal.

The PCR fragment was purified on a Biorad column and cut BamHI/SacII.

The plasmid pENI1861 (described in PCT/DK01/00805) was cut BamHI/SacII.

The PCR fragment and the plasmid vector was purified from a 1% gel.

Vector and PCR fragment was ligated O/N, and electrotransformed into the *E.coli* strain DH10B giving 123,000 independent *E.coli* transformants.

10 independent clones were sequenced and showed satisfactory diversity.

A DNA-prep was made from all the clones.

*Aspergillus* Transformation and Screening.

Approximately 5 μg DNA plasmid was transformed into Jal355 (as mentioned in WO 00/24883). After 20 minutes incubation with PEG, the protoplasts were washed twice with 1.2 M sorbitol, 10 mM Tris pH7.5 (to remove $CaCl_2$).

The protoplasts were mixed in an alginate-solution (1.5% alginate, 1% dextran, 1.2 M sorbitol, 10 mM Tris pH 7.5). Using a pump (Ole Dich 110ACR.80G38.CH5A), this alginate solution dripped into a $CaCl_2$-solution (1.2 M sorbitol, 10 mM Tris pH 7.5., 0.2 M $CaCl_2$) from a height of 15 cm. This created alginate beads of app. 2.5 mm in diameter with app. one transformed protoplast in every second bead. Approximately 55,000 transformants were generated.

After the beads had been made, they were transferred to 1.2 M sorbitol, 10 mM Tris pH7.5, 10 mM $CaCl_2$ and grown o/n at 30° C. The beads were washed twice with sterile water and afterwards transferred to 1*vogel (without a carbon source, which is already present in the alginate-beads (dextran)). The beads grew o/w at 30° C.

After o/w growth, the beads were spread on plates containing TIDE and olive oil (1 g/L agarose, 0.1 M Tris pH 9.0, 5 mM $CaCl_2$, 25 ml/L olive oil, 1.4 g/L TIDE, 0.004% brilliant green). The plates were incubated o/n at 37° C.

384 positive beads were transferred to four 96 well microtiter plates containing 150 μl 1*vogel, 2% maltose in each well.

The plates were grown for 3 days at 34° C.

Media was assayed for activity towards pnp-valerate and pnp-palmitate at pH7.5 (as described in WO 00/24883)). The 64 clones having the highest activity on the long-chained substrate (pnp-palmitate) as well as low activity on the short chained substrate (pnp-valerate) were isolated on small plates, from which they were inoculated into a 96 well microtiter plate containing 200 μl 1*vogel, 2% maltose in each well.

After growth for 3 days at 34° C. the media was once again assayed for activity towards pnp-valerate and pnp-palmitate at pH7.5, as well as activity towards pnp-palmiate at pH10.

10 clones showed fine activity at pH10 towards pnp-palmitate and poor activity at pH7.5 towards pnp-valerate.

Due to a deletion in the DNA oligo, one variant accidentally had 11 amino acid residues extra on the C-terminal rather than 3.

Identified positive in first round:

G91A+E99K+T231R+N233R+Q249R+270SVT

G91A+E99K+T231R+N233R+Q249R+270TPA

G91A+E99K+T231R+N233R+Q249R+270SVF

G91A+E99K+T231R+N233R+Q249R+270HTPSS-GRGGHR

The *Aspergillus* and screening procedure was repeated once again, thus identifying the following variants as positive:

G91A+E99K+T231R+N233R+Q249R+270LVY

G91A+E99K+T231R+N233R+Q249R+270EST

G91A+E99K+T231R+N233R+Q249R+270KV

G91A+E99K+T231R+N233R+Q249R+270RHT

G91A+E99K+T231R+N233R+Q249R+270TAD

Example 2

Evaluation of Odor and Wash Performance

The following lipase variants based on SEQ ID NO: 2 were evaluated:

N94K+D96L+T231R+N233R+Q249R30 270PGLPFKRV (SEQ ID NO: 15)

G91A+E99K+T231R+N233R+Q249R30 270AGVF (SEQ ID NO: 14)

G91A+E99K+T231R+N233R+Q249R30 270HTPSS-GRGGHR (SEQ IID NO: 13)

G91A+E99K+T231R+N233R+Q249R30 270HTPSS-GRGG (SEQ IID NO: 13)

G91A+E99K+T231R+N233R+Q249R30 270HTPSSGR (SEQ IID NO: 13)

G91A+E99K+T231R+N233R+Q249R30 270HTPSS (SEQ IID NO: 13)

G91A+E99K+T231R+N233R+Q249R+270HTP

G91A+E99K+T231R+N233R+Q249R+270SVF

G91A+E99K+T231R+N233R+Q249R+270LVY

G91A+E99K+T231R+N233R+Q249R+270EST

G91A+E99K+T231R+N233R+Q249R+270RHT

G91A+E99K+T231R+N233R+Q249R+270TAD

Washing tests were performed with cotton swatches soiled different soilings: lard/Sudan red and butter/Sudan red. The lard and butter swatches were heat treated at 70° C. for 25 minutes and cured overnight. The soiled swatches were washed for 20 minutes at 30° C. in a Terg-O-Tometer test washing machine in a wash liquor with 4 g/L of test detergent in water with hardness of 15° dH, followed by 15 minutes rinsing in tap water and drying overnight.

The lipase variant was added to the wash liquor at a dosage of 0.25 or 1.0 mg enzyme protein per liter. A control was made without addition of lipase variant, and a reference experiment was made with a lipase variant having the same amino acid sequence without any peptide extension.

The swatches were washed a second washing without lipase.

The performance was evaluated as follows:

Odor generation was evaluated by a sensory panel, keeping the washed butter swatches in closed vials until the evaluation.

Wash performance was evaluated by measuring the remission of the lard swatches after the first or the second washing. All variants showed a significant performance in this one-cycle washing test.

A benefit/risk ratio was calculated as the performance on lard swatches after the first or second washing divided by the odor on butter swatches. An improved benefit/risk ratio indicates that the lipase can be dosed at a higher level than the reference to give wash performance on level with the reference with reduced odor.

All variants tested showed lower odor generation and/or a higher benefit/risk ratio than the same lipase without a peptide extension at the C-terminal.

Example 3

First-wash Performance, Activity at Alkaline/Neutral pH, Long-chain/Short-chain Activity The following lipase variants based on SEQ ID NO: 2 were evaluated:

G91A+E99K+T231R+N233R+Q249R30 270HTPSS-GRGGHR (SEQ IID NO: 13)

G91A+E99K+T231R+N233R+Q249R30 270HTPSS-GRGG (SEQ IID NO: 13)

G91A+E99K+T231R+N233R+Q249R30 270HTPSSGR (SEQ IID NO: 13)

G91A+E99K+T231R+N233R+Q249R30 270HTPSS (SEQ IID NO: 13)

G91A+E99K+T231R+N233R+Q249R+270EST

The first-wash performance was evaluated as described above, and each lipase variant was found to give a remission increase (ΔR) above 3.0.

The lipase activity was determined as LU7, LU9 and SLU by the methods described above. Each lipase variant was found to have a LU9/LU7 ratio above 2.0 and a SLU/LU9 ratio above 2.0.

Original (for SUBMISSION) - printed on 07.02.2002 09:30:02 AM

| | | |
|---|---|---|
| **0-1** | **Form - PCT/RO/134 (EASY) Indications Relating to Deposited Microorganism(s) or Other Biological Material (PCT Rule 13bis)** | |
| 0-1-1 | Prepared using | PCT-EASY Version 2.92 (updated 01.01.2002) |
| **0-2** | **International Application No.** | PCT/DK02/00084 |
| **0-3** | **Applicant's or agent's file reference** | 10124-WO |

| | | |
|---|---|---|
| 1 | **The indications made below relate to the deposited microorganism(s) or other biological material referred to in the description on:** | |
| 1-1 | page | 2 |
| 1-2 | line | 13-19 |
| **1-3** | **Identification of Deposit** | |
| 1-3-1 | Name of depositary institution | DSMZ-Deutsche Sammlung von Mikroorganismen und Zellkulturen GmbH |
| 1-3-2 | Address of depositary institution | Mascheroder Weg 1b, D-38124 Braunschweig, Germany |
| 1-3-3 | Date of deposit | 08 February 2001 (08.02.2001) |
| 1-3-4 | Accession Number | DSMZ 14047 |
| **1-4** | **Additional Indications** | NONE |
| **1-5** | **Designated States for Which Indications are Made** | all designated States |
| **1-6** | **Separate Furnishing of Indications**<br>These indications will be submitted to the International Bureau later | NONE |
| 2 | **The indications made below relate to the deposited microorganism(s) or other biological material referred to in the description on:** | |
| 2-1 | page | 2 |
| 2-2 | line | 13-19 |
| **2-3** | **Identification of Deposit** | |
| 2-3-1 | Name of depositary institution | DSMZ-Deutsche Sammlung von Mikroorganismen und Zellkulturen GmbH |
| 2-3-2 | Address of depositary institution | Mascheroder Weg 1b, D-38124 Braunschweig, Germany |
| 2-3-3 | Date of deposit | 08 February 2001 (08.02.2001) |
| 2-3-4 | Accession Number | DSMZ 14048 |
| **2-4** | **Additional Indications** | NONE |
| **2-5** | **Designated States for Which Indications are Made** | all designated States |
| **2-6** | **Separate Furnishing of Indications**<br>These indications will be submitted to the International Bureau later | NONE |

Original (for SUBMISSION) - printed on 07.02.2002 09:30:02 AM

| | | |
|---|---|---|
| 3 | **The indications made below relate to the deposited microorganism(s) or other biological material referred to in the description on:** | |
| 3-1 | page | 2 |
| 3-2 | line | 13-19 |
| 3-3 | **Identification of Deposit** | |
| 3-3-1 | Name of depositary institution | DSMZ-Deutsche Sammlung von Mikroorganismen und Zellkulturen GmbH |
| 3-3-2 | Address of depositary institution | Mascheroder Weg 1b, D-38124 Braunschweig, Germany |
| 3-3-3 | Date of deposit | 08 February 2001 (08.02.2001) |
| 3-3-4 | Accession Number | DSMZ 14049 |
| 3-4 | **Additional Indications** | NONE |
| 3-5 | **Designated States for Which Indications are Made** | all designated States |
| 3-6 | **Separate Furnishing of Indications**<br>These indications will be submitted to the International Bureau later | NONE |
| 4 | **The indications made below relate to the deposited microorganism(s) or other biological material referred to in the description on:** | |
| 4-1 | page | 2 |
| 4-2 | line | 13-19 |
| 4-3 | **Identification of Deposit** | |
| 4-3-1 | Name of depositary institution | DSMZ-Deutsche Sammlung von Mikroorganismen und Zellkulturen GmbH |
| 4-3-2 | Address of depositary institution | Mascheroder Weg 1b, D-38124 Braunschweig, Germany |
| 4-3-3 | Date of deposit | 08 February 2001 (08.02.2001) |
| 4-3-4 | Accession Number | DSMZ 14051 |
| 4-4 | **Additional Indications** | NONE |
| 4-5 | **Designated States for Which Indications are Made** | all designated States |
| 4-6 | **Separate Furnishing of Indications**<br>These indications will be submitted to the International Bureau later | NONE |

FOR RECEIVING OFFICE USE ONLY

| | | |
|---|---|---|
| 0-4 | **This form was received with the international application:**<br>(yes or no) | yes |
| 0-4-1 | Authorized officer | |

FOR INTERNATIONAL BUREAU USE ONLY

| | | |
|---|---|---|
| 0-5 | **This form was received by the International Bureau on:** | |

Original (for SUBMISSION) - printed on 07.02.2002 09:30:02 AM

| | | |
|---|---|---|
| 0-5-1 | Authorized officer | |

The invention claimed is:

1. A method of producing a polypeptide having lipase activity comprising:

(a) culturing a cell comprising a nucleic acid sequence encoding a C-terminal extension linked to a nucleic acid sequence encoding a parent fungal polypeptide having lipase activity, wherein the amino acid sequence of the C-terminal extension is KV, EST, LVY, RHT, SVF, SVT, TAD, TPA, AGVF (SEQ ID NO: 14), or PGLPFKRV (SEQ ID NO: 15); and (b) recovering the polypeptide.

2. The method of claim 1, wherein the parent fungal polypeptide is a *Talaromyces* or *Thermomyces* polypeptide.

3. The method of claim 1, wherein the parent fungal polypeptide is a *Talaromyces thermophilus, Thermomyces ibadanensis, Talaromyces emersonii* or *Talaromyces byssochlamydoides* polypeptide.

4. The method of claim 1, wherein the parent fungal polypeptide has an amino acid sequence of SEQ ID NO: 2.

5. The method of claim 1, wherein the parent fungal polypeptide has an amino acid sequence of SEQ ID NO: 4.

6. The method of claim 1, wherein the parent fungal polypeptide has an amino acid sequence of SEQ ID NO: 6.

7. The method of claim 1, wherein the parent fungal polypeptide has an amino acid sequence of SEQ ID NO: 8.

8. The method of claim 1, wherein the parent fungal polypeptide has an amino acid sequence of SEQ ID NO: 10.

9. The method of claim 1, wherein the amino acid sequence of the C-terminal extension is KV.

10. The method of claim 1, wherein the amino acid sequence of the C-terminal extension is EST.

11. The method of claim 1, wherein the amino acid sequence of the C-terminal extension is LVY.

12. The method of claim 1, wherein the amino acid sequence of the C-terminal extension is RHT.

13. The method of claim 1, wherein the amino acid sequence of the C-terminal extension is SVF.

14. The method of claim 1, wherein the amino acid sequence of the C-terminal extension is SVT.

15. The method of claim 1, wherein the amino acid sequence of the C-terminal extension is TAD.

16. The method of claim 1, wherein the amino acid sequence of the C-terminal extension is TPA.

17. The method of claim 1, wherein the amino acid sequence of the C-terminal extension is AGVF (SEQ ID NO: 14).

18. The method of claim 1, wherein the amino acid sequence of the C-terminal extension is PGLPFKRV (SEQ ID NO: 15).

* * * * *